(12) United States Patent
Chu et al.

(10) Patent No.: US 6,235,517 B1
(45) Date of Patent: May 22, 2001

(54) PHYTASE-PRODUCING BACTERIA, PHYTASE AND PRODUCTION METHOD OF PHYTASE

(75) Inventors: Jaw-Shiow Chu; Su-Fang Chung; Min Tseng; Chiou-Yen Wen; Wen-Shen Chu, all of Hsin-Chu (TW)

(73) Assignee: Food Industry Research & Development Institute, Hsin-Chu (TW)

( * ) Notice: Subject to any disclaimer, the term of this patent is extended or adjusted under 35 U.S.C. 154(b) by 0 days.

(21) Appl. No.: 09/436,490

(22) Filed: Nov. 9, 1999

Related U.S. Application Data

(62) Division of application No. 09/038,705, filed on Mar. 9, 1998, now abandoned.
(60) Provisional application No. 60/057,780, filed on Sep. 8, 1997.

(30) Foreign Application Priority Data

Mar. 7, 1997 (TW) ................................................ 86102894

(51) Int. Cl.$^7$ ............................... C12N 1/12; C12N 1/20; C12N 1/36
(52) U.S. Cl. ........................ 435/252.1; 435/243; 435/245
(58) Field of Search ................................ 435/252.1, 243, 435/245

(56) References Cited

U.S. PATENT DOCUMENTS 6,033,897 * 3/2000 Chu et al. .

FOREIGN PATENT DOCUMENTS 0 420 358   4/1991 (EP) .

OTHER PUBLICATIONS

Wim van Hartingsveldt, Cora M.J. van Zeijl, G. Marian Harteveld, Robin J. Gouka, Marjon E.G. Suykerbuyk, Ruud G. M. Luiten, Peter A. van Paridon, Gerard C.M. Selten, Annemarie E. Veenstra, Robert F.M. van Corcom and Cees A.M.J.J. van den Hondel, Cloning, characterization and overexpression of the phytase–encoding gene (phyA) of *Aspergillus niger*, Jan. 6, 1993, pp. 87–94.

Joseph A. Maga, Journal of Agricultural and Food Chemistry, Jan. 1/Feb. 1982, vol. 30, No. 1, pp. 1–9.

Gerard A. Walsh, Ronan F. Power and Denis R. Headon, Enzymes in the animal–feed industry, Mar. 1994, vol. 5, p. 81–87.

Rudy J. Wodzinski and A.H. Ullah, Phytase, Department of Molecular Biology and Microbiology University of Central Florida, 1196, pp. 265–302.

Luis Pasamontes, Monika Haiker, Markus Wyss, Michel Tessier, and Adolphus P.G.M. van Loon, Gene Cloning, Purification, and Characterization of a Heat–Stable Phytase from the Fungus *Aspergillus fumigatus*, Feb. 10, 1997, pp. 1696–1700.

Abul H.J. Ullah and H. Charles Dischinger, Jr., *Aspergillus ficuum* Phytase: Complete Primary Structure Elucidatin By Chemical Sequencing, Mar. 15, 1993, pp. 747–753.

David B. Mitchell, Kurt Vogel, Bernd J. Weimann, Luis Pasamontes and Adolphus P.G.M. van Loon, (1997), The phytase subfamily of histidine acid phosphatases:isolation of genes for two novel phytases from the fungi *Aspergillus terreus* and *Myceliophthora thermophila*, pp. 245–252.

* cited by examiner

Primary Examiner—Lynette R. F. Smith
Assistant Examiner—Li Lee
(74) Attorney, Agent, or Firm—Sughrue, Mion, Zinn, Macpeak & Seas, PLLC

(57) ABSTRACT

This invention relates to the isolation of thermophilic phytase-producing microorganisms, method for producing phytase using such microorganisms, phytase obtained therefrom, and usage of the phytase to hydrolyze phytic acid or phytate. In particular, this invention relates to phytase-producing microorganisms, which belong to Streptomyces sp., Pseudonocardia sp. or Microbispora sp., and which produce phytase available for recovery in an efficient and practical manner.

1 Claim, 1 Drawing Sheet

PHYTASE-PRODUCING BACTERIA, PHYTASE AND PRODUCTION METHOD OF PHYTASE

CROSS REFERENCE TO RELATED APPLICATIONS

Figure 1:
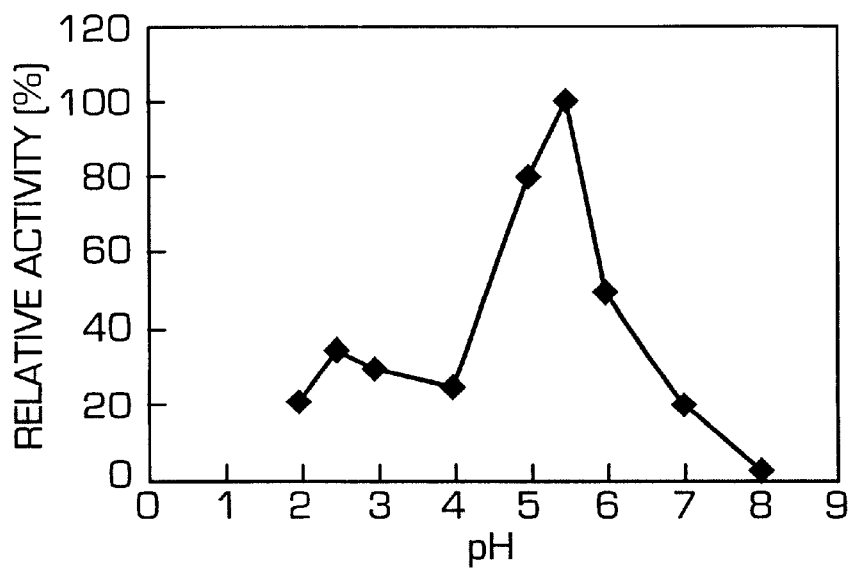

This application is a divisional application of parent application Ser. No. 09/038,705, filed Mar. 9, 1998, now abandoned the disclosure of which parent application Ser. No. 09/038,705 is incorporated herein by reference. Also, this application through parent application Ser. No. 09/038, 705 claims benefit under 35 U.S.C. §119(e) to earlier filed provisional application 60/057,780, filed Sep. 8, 1997.

FIELD OF INVENTION

This invention relates to the isolation of thermophilic phytase-producing microorganisms, method for producing phytase using such microorganisms, phytase obtained therefrom, and usage of the phytase to hydrolyze phytic acid or phytate. In particular, this invention relates to phytase-producing microorganisms, which belong to *Streptomyces sp., Pseudonocardia sp.* or *Microbispora sp.,* and which produce phytase available for recovery in an efficient and practical manner.

BACKGROUND OF THE INVENTION:

Phytic acid (myoinositol 1,2,3,4,5,6-hexakis dihydrogen phosphate) is known as one of the major component of plant-derived food. It is the primarily source of inositol and the main storage form of phosphorus in plant seeds that are used as animal feed ingredients (oilseed meals, cereal grains, and legumes). Approximately 75% of the total phosphorus in cereals, legumes and seeds exist as phytic acid phosphorus. When one or more of the acidic protons of the phophate groups in phytic acid are replaced by a counterion, the compound is usually referred to as a phytate salt. The name phytin is used for the calcium-magnesium salt of phytate derived from plant seeds (a discontinued product of Ciba-Geigy).

Phytic acid plays an important role in the dormacy and germination stages of plant seeds. It was believed that phosphorus was liberated on germination and incorporated into ATP. Recent studies have estblished the role of inositol phosphate intermediates in the transport of materials into cells and their role in transport as secondary messengers and in signal transduction in plant and animal cells is a very active area of research.

There are many applications of phytic acid, including industrial use as a corrosion inhibitor on metals, a rust remover and an additive to lubricating greases, use as a food additive, and medical applications, including use in the prevention of dental caries, use as an imaging agent for organ scintography and an X-ray enhancement contrasting agent, use as a hypocholestromic agent, use to reduce gastric secretion for treatment of gastritis, gastroduodenitis, gastric duodenal ulcers and diarrhea, use as an antidote for toxic metal absorption, therapeutic uses in the prevention and dilution of calcium deposits associated with various diseases and for reducing calcium concentration in urine (thus checking the formation of renal calculi), use as a preventive agent against severe poisoning with pressurized oxygen and preventing thirst during exercise, use as a taste-improving agent in orally administered antibiotics, and use in the treatment of multiple sclerosis (see U.S. Pat. No. 5,217,959 issued to Robert Sabin). For further discussions of industrial applications of phytic acid, see Graf, JAOCS 60, 1861–1867, 1983.

Phytic acid may be prepared in pure form from various plant sources, such as wheat, corn, soybeans, sesame seeds, peanuts, lima beans, barley, oats, wild rice and sunflower seeds, and it can be extracted with dilute hydrochloric acid at room temperature, precipitated with various reagents including ferric chloride, bicarbonates, potassium hydroxide, sodium hydroxide, ammonium hydroxide, calcium hydroxide, magnesium hydroxide or alcohol. It is then further purified by conventional chemical techniques. Hydrolyis of phytic acid and phytates may be carried out by partial acid or basic hydrolysis or by hydrolysis using phytase, and the resultant products include phosphate, inositol and various inositol phosphate intermediates.

Phytic acid phosphorus has anti-nutritive properties as it is essentially poorly metabolized by monogastric animals, such as pourltry and swine, because these animals produce little or no phytase in their digestive tracts. In addition, phytic acid forms complexes with proteins and divalent cations, such as calcium, iron, zinc, magnesium, manganese, copper and molybdenum. Phytic acid also binds to starch and influences the digestibility and solubility or starch. Phytic acid excreted in the manure of feed animals is enzymatically hydrolyzed by soil and water microorganisms. The released phosphorus is transported into rivers and lakes and if introduced in high qunatities causes eutrophication. The anti-nutritive properties and its valus as a possible pohosphorus source, have stimulated researchers to develop a method to remove phytic acid in a manner that is economically competitive wuth mineral supplementation.

Hydrolyzing phytic acid is thought to be a useful way of increasing the nutritional value of many plant foodstuffs. The enzymes that catalyze the conversion of phytic acid to inositol and inorganic phosphate are known as phytases. Phytase is found to be distributed in the seeds and pollens of plants, and also some microorganisms. The mass production of phytase from plant origin is not economic since preliminary treatment is necessary and the production procedure becomes time-comsuming, troublesome and expensive. Therefore, the production of phytase from microbial origin is of greater potential in development. The feeding of microbial phytase to monogastric animals alter the phytic acid complexes and increase the bioavailability of phosphorus, calcium and probably proteins to monogastric animals.

The research of phytase spans more than 87 years from its discovery by Suzuki et al. (Tokyo Imp. Univ. Coll. Agr. Bull., 7: 503–512, 1907) until its commercialization in Europe in 1993–1994 by Gist-brocades. The international Union of Biochemistry (1979) lists two phytase: a 3-phytase, EC 3.1.3.8, which hydrolyzes the ester bond at the 3-position of myoinositolhexakus phosphate to D-myoinositol 1,2,4,5,6-pentakisphosphate+ orthophosphate, and a 6-phytase, EC 3.1.3.26, which first phdrolyzes the 6-position of myoinositolhexakus phosphate to D-myoinositol 1,2,3,4,5-pentakis-phosphate+ orthophosphate. Subsequent ester bonds in the substrate are hydrolyzed at different rates. The 6-phytase dephosphorylates phytic acid completely, whereas the aforesaid 3-phytase does not hydrolyze the phosphomono ester.

Currently, phytase-producing microorganisms include bacteria, such as *Bacillus subtilis* and *Escherichia coli;* yeasts, such as *Saccharomyces cerevisias* and *Schwannoiomyces castellii;* and fungi, such as *Aspergillus niger, A. oryzae, A. ficuum, Penicillium simplicissimum.*

Yeasts produce phytase intracellularly and, hence, it is difficult and less efficient to recover phytase with a high yield.

Of all the microorganisms surveyed, Aspergillus niger (syn. A. ficuum) NRRL 3135 produces phytase extracelllularly, and the phytase produced thereby is known to be most active and has been commercialized. The microorganism is subjected to solid state fermentation (SSF) together with cereal grains, legume beans or foodstuffs so as to substantially remove or reduce phytic acid therefrom.

A thorough review of the research and development of phytase is provided by Rudy J. Wodzinski et al., in "Phytase," *Advances in Applied Microbiology,* Vol. 42, p. 263–303, 1996, and other relevant docuementary references are cited in the Reference List accompanying the Specification.

However, since during fermentation, the temperature within the fermenter normally will rise to 55° C. or higher, the efficiacy of removing phytic acid by microbial fermentation using non-thermophilic microorganisms is significantly decreased. In addition, fungal cells grow slowly and hence, it takes longer time (about 10 days) for the fungal cells to produce phytase having high enzymatic activity.

There thus still exists a need to produce phytase by a phytase-producing microorganism which is thermophilic and which maintains the ability to remove phytic acid during solid state fermentation. The industrial application of such a phytase-producing microorganism is promising as the phytase produced thereby is thermostable and fermentation using the same is efficient and energy saving.

SUMMARY OF THE INVENTION

An object of this invention is to isolate a thermophilic microorganism which produced phytase extracellularlly and which can be used in large-scale solid state fermentation for the industrial production of phytase.

Another object of this invention is to industrially produce phytase by using said thermophilic microorganism in large-scale solid state fermentation.

Heretofore, it has not been reported that actinomycetes produce phytase.

The present invention screened and obtained 14 microbial Isolates which are thermophilic and produce phytase extracellularlly. These isolates include *Streptomyces thermoviolaceus* subsp. thermoviolaceus CCRC 12493, *Streptomyces thermodiastaticus* CCRC 12492 and *Streptomyces thermoviolaceus* subsp. thermoviolaceus CCRC 12639, the three isolates being microorganisms listed in the Catalogue of bacteria, Bacteriophages & Recombinant DNA Materials published by the Food Industry Research and Development Institute (FIRDI), Hsin-Chu, Taiwan, R.C.C., isolate T16-4 (*Streptomyces thermonitrificans*), isolate T17-1 (*Streptomyces thermonitriticans*), isolate T17-2 (*Streptomyces thermovulgaris*), T17-4 (*Pseudonocardia thermophila*), isolate T17-6 (*Pseudonocardia thermophila*), isolate T19-3 (Streptomyces sp.), isolate T24-3 (*Streptomyces diastaticus*), isolate T26-6 (Streptomyces sp.), isolate T28-1 (Streptomyces sp.), isolate T29-1 (Microbispora sp.), and isolate T45-1 (*Streptomyces aurantiogriseus*), the eleven isolates having been deposited in the China Center for Type Culture Collection (CCTCC), Wuhan University, Luo Jia Shan, Wuhan, the People's Republic of China under the Budapest Treaty for the purposes of patent applications on Sep. 29, 1997 with the accession numbers of CCTCC M97007, CCTCC M97008, CCTCC M97009, CCTCC M970010, CCTCC M970011, CCTCC M970012, CCTCC M970013, CCTCC M970014, CCTCC M970015, CCTCC M970016 and CCTCC M970017, respectively. Isolates T16-4, T24-3 and T45-1 were also deposited in the FIRDI for the purpose of patent application on Mar. 6. 1997 with the accession numbers of CCRC 910076, CCRC 910075 and CCRC 910074, respectively.

Figure 2:
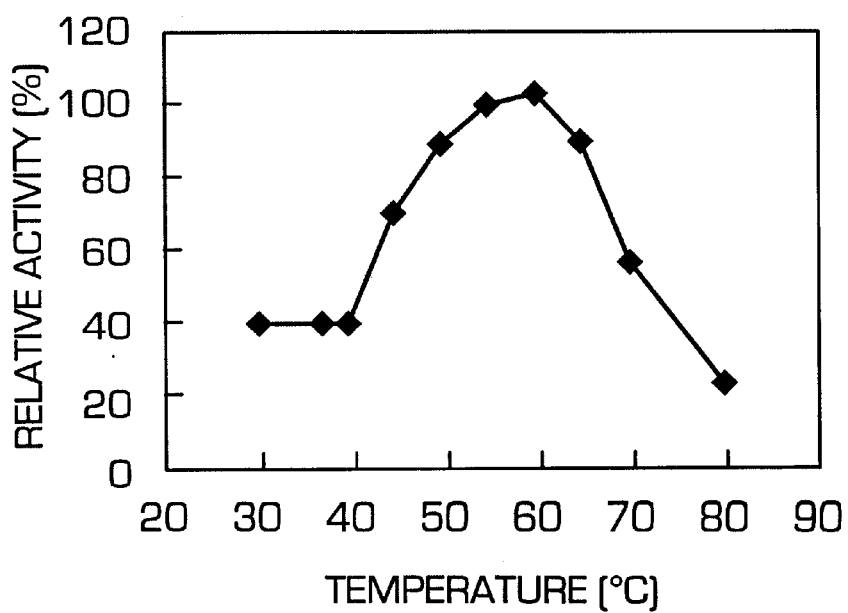

Features and advantages of the present invention will become apparent in the following detailed description of the examples, with reference to the accompanying drawings, of which:

BRIEF DESCRIPTIONS OF THE DRAWINGS:

FIG. 1 is a graph showing the influence of pH to the enzyme activity of phytase produced by isolate T17-2; and FIG. 2 is a graph showing the influence of temperature to the enzyme activity of phytase produced by isolate T17-2.

EXAMPLES

A. METHODS AND MATERIALS

Medium: The formulation of the phytase screen medium (PSM) is shown below:

| | |
|---|---|
| 1.5% | glucose |
| 0.5% | $NH_4NO_3$ |
| 0.05% | KCl |
| 0.05% | $MgSO_4 \cdot 7H_2O$ |
| 0.001% | $FeSO_4 \cdot 7H_2O$ |
| 0.001% | $MnSO_4 \cdot 7H_2O$ |
| 0.05% | Ca-phytate |
| 2.0% | agar |
| adjust pH to 5.5 | |

I. Cultivation of phytase-producing microorganisms:

The microorganism to be screened is cultivated in TSB medium (15 g/L tryptone, 5.0 g/L soybtone, 5.0 g/L NaCl, 1.0 L distilled water) at 45° C. overnight. 0.1 ml of the cultivated mcroorganism is collected and inoculated into 50 ml PSM broth, allowing the microorganism to grow at 45° C. for 4 days with agitation at a rate of 125 rpm.

II. Screening of phytase-producing microorganisms:

Isolation of the phytase-producing microorganism is carried out by: sampling soil from the south part of Taiwan, subjecting the soil samples to HV medium (1 g/L humic acid, 0.5 g/L $Na_2HPO_4$, 1.7 g/L KCl, 0.05 g/L $MgSO_4 \cdot 7H_2O$, 0.02 g/L $CaCO_3$, B-vitamin, agar 18 g/L), and cultivating the samples at 50° C. to screen isolates which produce phytase extracellularly. Streptomytes deposited in the FIRDI, Taiwan, R.O.C. are also screened concomitantly in a same manner to collect those strains which are phytase-producing.

III. Detection of the enzymatic activity of phytase:

The phytase activity is detected by the following method:

1. Inoculate the isolate into a 50 ml PSM broth (substituting 0.05% Ca-phytate with 0.01% Na-phytate), cultivate the isolate at 45° C. for 4 days, and centrifugate the isolate at 3000 rpm for 5 minutes, the supernatant being collected as an enzyme solution;

2. Preparation of enzyme substrate: dissolve 1.64 g of Na-phytate in 0.25 M sodium acetate buffer (pH 5.5).

dissolve 1.64 g of Na-phytate in 0.25M glycine-HCl buffer (pH 2.5).

3. 1 ml enzyme solution is added with 1 ml enzyme substrate, allows the mixture to react at 55° C. for 60 minutes, and 10% trichloroacetic acid (TCA) is added into the mixture to stop reaction. Adds 2 ml color developing agent (3.66 g $FeSO_4$-$7H_2O$, 0.5 g ammonium heptamolybdate tetrahydrate, 1.6 ml conc. $H_2SO_4$, adding $H_2O$ to 50 ml) into the mixture and detect the absorbance at 750 nm. The calibration curve is made with use of $NaH_2PO_4$. A unit of phytase activity is defined as 1 $\mu$mol phosphate produced by 1 ml enzyme solution per minute.

B. RESULTS:

The soil samples are cultured in PSM at 50° C. for 7 days, and microbial colonies which are surrounded with a clear zone on the culture plates are isolated and screened.

150 microbial isolates which are derived from the soil samples of the south part of Taiwan and 30 actinomycete strains deposited in the FIRDI are cutivated in PSM to screen microorganisms which are thermophilic and produce phytase extracellularly. These microorganisms are inoculated into 50 ml PSM broth and grow at 45° C. for 4 days with agitation at at rate of 125 rpm. The microbial cultures are centrifugated at 3000 rpm and the supernatants are collected. The phytase activity is respectively detected under pH 5.5 at a temperature of 55° C. and under pH 2.5 at a temperature of 55° C.

The enzyme activity of phytase produced by the obtained 14 isolates and the sources of these isolates are shown in Table 1.

The detected enzyme activity of phytase produced by isloate T45-1 is $8.9 \times 10^4$ U/ml under pH 5.5 at a temperature of 55° C. and $2.5 \times 10^{-4}$ U/ml under pH 2.5 at a temperature of 55° C., respectively.

The detected enzyme activity of phytase produced by isloate T24-3 is $5 \times 10^{-6}$ U/ml under pH 5.5 at a temperature of 55° C. and $1 \times 10^{-5}$ U/ml under pH 2.5 at a temperature of 55° C., respectively.

The detected enzyme activity of phytase produced by isloate T16-4 is $3.8 \times 10^{-4}$ U/ml under pH 5.5 at a temperature of 55° C. and $1.1 \times 10^{-5}$ U/ml under pH 2.5 at a temperature of 55° C., respectively.

The detected enzyme activity of phytase produced by Streptomyces thermoviolaceus subsp. thermoviolaceus CCRC 12493, is $1.8 \times 10^{-3}$ U/ml under pH 5.5 at a temperature of 55° C. and $2.5 \times 10^{-4}$ U/ml under pH 2.5 at a temperature of 55° C., respectively.

The detected enzyme activity of phytase produced by Streptomyces thermodiastaticus CCRC 12492 is $2 \times 10^{-4}$ U/ml under pH 5.5 at a temperature of 55° C. and $3.1 \times 10^{-4}$ U/ml under pH 2.5 at a temperature of 55° C., respectively.

The detected enzyme activity of phytase produced by Streptomyces thermoviolaceus subsp. thermoviolaceus CCRC 12639 is $1.1 \times 10^{-4}$ U/ml under pH 5.5 at a temperature of 55° C. and $9.3 \times 10^{-5}$ U/ml under pH 2.5 at a temperature of 55° C., respectively.

Further ioslates are obtained from the same screening procedure and they are isolates T17-1, T17-2, T17-4, T17-6, T19-3, T26-6, T28-1 and T29-3.

The detected enzyme activity of phytase produced by isloate T17-2 is $2.2 \times 10^{-3}$ U/ml under pH 5.5 at a temperature of 55° C. and $2.8 \times 10^{-4}$ U/ml under pH 2.5 at a temperature of 55° C. It is T17-2 is 5.7 U/mil under pH 5.5 at a temperature of 55° C. It is found that when the pH and temperature for the enzyme activity analysis are varied, the produced phytase is most active at pH 5.5 (FIG. 1) and the optimal temperature for the enzyme is in the range from 55° C. to 60° C., with 90% activity being maintained at 65° C. (FIG. 2). In addition, when isolate T17-2 is cultivated in media supplemented with different carbon and nitrogen sources, the produced phytase is most active when the isolate is cultivated in a medium containing 1.5% glucose and 0.5% $KH_4NO_3$ (Table 2).

The obtained microbial isolate T45-1 has the following taxonomic features:

1. gram-positive, 2. aerial mycelium, 3. the spore surface is smooth and the spore chain is in spiral form, 4. the cellular hydrolysates include L,L-diaminopimelic acid and no specific sugar is present on the cell wall of the microorganism, 5. colonies with wrinkled surface are present on the HV plate.

Based on the above features, isolate T45-1 is determined and classified as a *Streptomyces auranthigriseus* according to the Bergey's Manual of Systematic Bacteriology.

The obtained microbial isolate T24-3 has the following taxonomic features:

1. gram-positive, 2. aerial mycelium, 3. the spore surface is smooth and the spore chain is in spiral form, 4. the cellular hydrolysates include L,L-diaminopimelic acid and no specific sugar is present on the cell wall of the microorganism, 5. growth temperature: 30° C. to 49° C.

6. colonies carrying grey-black spores on the surface are present on the HV plate.

Based on the above features, isolate T24-3 is determined and classified as a *Streptomyces diastaticus* according to the Bergey's Manual of Systematic Bacteriology.

The obtained microbial isolate T16-4 has the following taxonomic features:

1. gram-positive,
2. aerial mycelium,
3. the spore surface is smooth and the spore chain is in spiral form,
4. the cellular hydrolysates include L,L-diaminopimelic acid and no specific sugar is present on the cell wall of the microorganism,
5. growth temperature: 30° C. to 49° C.
6. colonies carrying white spores are present on the HV plate.

Based on the above features, isolate T16-4 is determined and classified as a *Streptomyces thermmonitrificans* according to the Bergey's Manual of Systematic Bacteriology.

The obtained microbial isolate T17-1 has the following taxonomic features:
1. gram-positive,
2. aerial mycelium,
3. the spore surface is smooth and the spore chain is in spiral form,
4. the cellular hydrolysates include L,L-diaminopimelic acid and no specific sugar is present on the cell wall of the microorganism,
5. growth temperature: 30° C. to 49° C.

Based on the above features, isolate T17-1 is determined and classified as a *Streptomyces thermmonificans* according to the Bergey's Manual of Systematic Bacteriology.

The physiological and biochemical characters of the eleven isolates obtained in this invention are analysed and listed in Table 3, and a comparison of the same with reference strains, which are known standard microorganism strains deposited in the FIRDI and the scientific names of which are listed in Table 4, is made and listed in Table 5. From the comparison with the reference strains, the taxons of these isolates are determined and listed in Table 6.

With respecpect to isolates T17-4 and T17-6, since the two isolates are analogous to *Pseudonocardia theremophila* in terms of morphology and fatty acid contents (see Tables 7 and 8), they are subjected to G+C content analysis and DNA hybridization test. The two isolates are found to respectively have a G+C percentage of 74% and 75.2%, and their DNA hybridization results show a homology greater than 98%. Therefore, isolates T17-4 and T17-6 are classified as *Pseudonocardia theremophila*.

From the above teachings, it is apparent that various modifications and variations can be made without departing from the psirit and scope of the present invention. It is therefore to be understood that this invention may be practiced otherwise than as specifically described.

TABLE 1

The phytase activities and isolation sources of the obtained phytase-producing isolates

| ISOLATE NO. | PHYTASE ACTIVITY(U/ml) AT 55° C. | SOURCE |
|---|---|---|
| T17-2 | $2.2 \times 10^{-3}$ | goat manure |
| T19-3 | $2.1 \times 10^{-3}$ | soil |
| T29-1 | $1.9 \times 10^{-3}$ | soil |
| CCRC12639 | $1.1 \times 10^{-4}$ | FIRDI |
| CCRC12493 | $1.8 \times 10^{-3}$ | FIRDI |
| T28-1 | $9.1 \times 10^{-4}$ | soil |
| T45-1 | $8.9 \times 10^{-4}$ | soil |
| T17-1 | $8.8 \times 10^{-4}$ | goat manure |
| T26-6 | $8.5 \times 10^{-4}$ | soil |
| CCRC12492 | $8.2 \times 10^{-4}$ | FIRDI |
| T24-3 | $5 \times 10^{-4}$ | soil |
| T16-4 | $3.8 \times 10^{-4}$ | soil |
| T17-6 | $3.1 \times 10^{-4}$ | goat manure |
| T17-4 | $3.6 \times 10^{-4}$ | goat manure |

TABLE 2

The phytase activities of the T17-2 incubated at different carbon and nitrogen sources.

| C source (1.5%) | Activity ($10^{-3}$ U/ml at 55° C.) | N source (0.5%) | Activity ($10^{-3}$ U/ml at 55° C.) |
|---|---|---|---|
| glucose | 5.6 | $NH_4NO_3$ | 5.6 |
| sucrose | 3.5 | yeast extract | 1.3 |
| xylose | 1.2 | polypeptone | 1.9 |
| arabinose | 1.2 | $(NH_4)_2SO_4$ | 0.8 |
| lactose | 0.5 | $KNO_3$ | 2.5 |
| maltose | 1.5 | urea | 0.9 |
| corn starch | 0.8 | glycine | 0.5 |
| soluble starch | 2.8 | | |
| mannitol | 0.5 | | |

TABLE 3

The physiological and biochemical character analyses of the obtained phytase-producing isolates

| Isolate Analysis items | T16-4 | T17-1 | T17-2 | T17-4 | T17-6 | T19-3 | T24-3 | T26-6 | T28-1 | T29-1 | T45-1 |
|---|---|---|---|---|---|---|---|---|---|---|---|
| Utility of | | | | | | | | | | | |
| Arabinose | − | − | + | Nd. | Nd. | − | − | +/− | − | + | + |
| Cellulose | − | − | − | + | + | − | − | − | − | − | − |
| Fructose | − | + | − | − | − | − | − | − | − | − | + |
| Inositol | + | + | + | + | + | +/− | +/− | +/− | − | − | + |
| Lactose | + | + | − | + | + | − | − | − | + | + | + |
| Mannitol | − | + | − | − | − | + | + | + | + | + | + |
| Raffinose | − | − | − | + | + | − | − | + | + | − | + |

TABLE 3-continued

The physiological and biochemical character analyses of the obtained phytase-producing isolates

| Isolate Analysis items | T16-4 | T17-1 | T17-2 | T17-4 | T17-6 | T19-3 | T24-3 | T26-6 | T28-1 | T29-1 | T45-1 |
|---|---|---|---|---|---|---|---|---|---|---|---|
| Rhamnose | − | − | − | + | + | − | − | − | + | + | + |
| Salicin | − | + | − | − | + | − | − | − | − | − | + |
| Sucrose | − | − | − | − | − | − | − | − | − | + | + |
| Xylose | − | + | + | − | − | + | + | + | + | + | + |
| Degradation of | | | | | | | | | | | |
| Adenine | − | − | − | − | − | − | − | + | + | − | + |
| Caseine | + | + | + | Nd. | Nd. | + | + | + | + | + | + |
| Esculin | − | + | − | − | − | − | − | + | + | − | + |
| Hypoxanthine | + | − | − | − | − | − | + | + | + | − | + |
| L-tyrosine | + | + | + | + | + | + | + | +(dark[a]) | +(dark[a]) | − | + |
| Xanthine | + | − | − | − | − | − | − | − | − | − | + |
| Lysozyme | − | − | − | − | − | − | − | − | − | − | − |
| Urease | − | − | − | + | + | − | − | − | − | − | − |

Nd: :not determined
[a]producing melanin in broth

TABLE 4

Scientific name list of the Standard strains deposited in the FIRDI

| Standard strain no. | Scientific name |
|---|---|
| CCRC10433 = ATCC23916 | S. griseofuscus |
| CCRC11465 = ATCC19743 | S. collinus |
| CCRC12034 = ATCC29251 | S. longwoodensis |
| CCRC12068 = ATCC25453 | S. flocculus |
| CCRC12169 = ATCC11874 | S. cinnainoneus |
| CCRC12492 = NRRL B-5316 | S. thermodiasticus |

TABLE 4-continued

Scientific name list of the Standard strains deposited in the FIRDI

| Standard strain no. | Scientific name |
|---|---|
| CCRC12493 = NRRL 12374 | S. thermoviolaceus |
| CCRC12636 = ATCC27472 | S. thermodiastaticus |
| CCRC12638 = ATCC19284 | S. thermovulgaris |
| CCRC12639 = ATCC19283 | S. thermoviolaceus subsp. thermoviolaceus |
| CCRC13311 = ATCC 15723 | S. poonensis |

The results of biophysical and biochemical character of type strains of streptomyces

| Type strain Analysis items | CCRC10483 | CCRC12034 | CCRC12068 | CRRC11465 | CCRC12169 | CCRC12492 |
|---|---|---|---|---|---|---|
| Utility of | | | | | | |
| Arabinose | + | − | + | + | − | − |
| Cellulose | − | − | − | − | − | − |
| Fructose | + | − | + | − | − | − |
| Inositol | − | + | + | + | − | − |
| Lactose | − | + | + | − | + | + |
| Mannitol | − | − | + | + | − | + |
| Raffinose | − | − | − | + | − | − |
| Rhamnose | − | − | + | − | − | − |
| Salicin | − | − | + | − | − | − |
| Sucrose | − | − | − | + | − | − |
| Xylose | + | + | − | − | − | + |
| Degradation of | | | | | | |
| Adenine | + | + | + | + | − | + |
| Hypoxanthine | + | + | + | + | + | − |
| L-tyrosine | + | + | + | + | + | +(dark[a]) |
| Xanthine | + | − | + | + | − | − |
| Caseine | + | + | + | + | − | + |
| Esculin | + | + | − | − | − | + |
| Lysozyme | − | − | − | − | + | − |
| Urease | − | − | + | − | − | − |

-continued

| Type strain Analysis items | CCRC12493 | CCRC12636 | CCRC12638 | CCRC12639 | CCRC13311 |
|---|---|---|---|---|---|
| Utility of | | | | | |
| Arabinose | − | − | + | − | + |
| Cellulose | − | − | − | − | + |
| Fructose | − | − | + | − | − |
| Inositol | − | − | + | + | + |
| Lactose | − | + | − | − | + |
| Mannitol | + | + | + | − | + |
| Raffinose | − | + | − | − | − |
| Rhamnose | − | − | − | − | − |
| Salicin | − | − | − | − | + |
| Sucrose | − | − | − | − | − |
| Xylose | + | + | + | − | + |
| Degradation of | | | | | |
| Adenine | + | + | + | + | + |
| Hypoxanthine | + | − | − | − | + |
| L-tyrosine | +(dark[a]) | +(dark[a]) | +(dark[a]) | +(dark[a]) | + |
| Xanthine | − | − | − | − | + |
| Caseine | + | + | + | + | − |
| Esculin | + | + | + | + | − |
| Lysozyme | − | − | − | − | − |
| Urease | − | − | − | − | + |

TABLE 6

The identified names of the obtained phytase-producing isolates

| Isolate no. | Identified results |
|---|---|
| T16-4 | Streptomyces thermonitrificans |
| T17-1 | Streptomyces thermonitrificans |
| T17-2 | Streptomyces thermovulgaris |
| T17-4 | Pseudonocardia thermophila |
| T17-6 | Pseudonocardia thermophila |
| T19-3 | Streptomyces sp. |
| T24-3 | Streptomyces diastaticus |
| T26-6 | Streptomyces sp. |
| T28-1 | Streptomyces sp. |
| T29-1 | Microbispora sp. |
| T45-1 | Streptomyces aurantiogriseus |

TABLE 7

The fatty acid content of isolate T17-6
Strain: T17-6

| fatty acid species | content (%) |
|---|---|
| 15:0 ISO | 2.54 |
| 16:0 ISO | 28.6 |
| 16:0 | 3.8 |
| ISO 17:1 w9c | 3.18 |
| 17:0 ISO | 24.27 |
| 17:0 ANTEISO | 17.40 |
| 17:0 | 2.76 |
| 17:1 w6c | 1.71 |
| 17:0 | 2.76 |
| 16:1 2OH | 3.77 |
| 17:0 10 methyl | 0.89 |
| 18:0 ISO | 6.09 |
| 18:0 | 3.45 |
| 19:0 ANTEISO | 0.63 |

TABLE 8

The fatty acid content of isolate T17-4
Strain: T17-4

| fatty acid species | content (%) |
|---|---|
| 14:0 ISO | 0.4 |
| 15:0 ISO | 3.76 |
| 15:0 ANTEISO | 0.34 |
| 15:0 | 0.41 |
| ISO 16:1 ISO H | 0.33 |
| 16:0 ISO | 36.01 |
| 16:0 | 2.71 |
| ISO 17:1 w9c | 5.55 |
| 17:0 ISO | 20.13 |
| 17:0 ANTEISO | 14.91 |
| 17:1 w8c | 0.55 |
| 17: w6c | 3.00 |
| 17:0 | 1.97 |
| 16:1 2OH | 3.51 |
| 17:0 10 methyl | 1.18 |
| 18:0 ISO | 4.17 |
| 19:0 ANTEISO | 0.2 |

REFERENCE LIST:

1. Rudy J. Wodzinski et al., "Phytase," Advances in Applied Microbiology, Vol. 42, p. 263–303, 1996.

2. T. R. Shieh et al., Applied Microbiology, Vol. 16 (9), p.1348–1351, 1968.

3. Laurent Seaueilha et al., J. Agri. Food. Chem., Vol. 41, p. 2451–2454, 1993.

4. Marisa K. Chelius et al., Applied Microbiology and Biotechnology, Vol. 41, p. 79–83, 1994.

5. V. C. Nair et al., Applied Microbiology and Biotechnology, Vol. 34, p. 183–188, 1990.

6. Seong Jun Yoon et al., Enzyme and Micorbial Technology, Vol. 18, p. 449–454, 1996.

7. Wim van Hartingsveldt et al., Gene, Vol. 127, p. 87–94, 1993.

8. Christel Lambrechts et al., Biotechnology Letters, Vol. 14 (1), p. 61–66, 1992.

9. David B. Mitchell et al., Microbiology, Vol. 143, p. 245–252, 1997.

10. U.S. Pat. No. 5,217,959.

What is claimed is:

1. A microbial isolate T29-1, which is classified as Microbispora sp. and deposited in the China Center for Type Culture Collection (CCTCC), Wuhan University, Luo Jia Shan, Wuhan, the People's Republic of China on Sep. 29, 1997 with the accession number of CCTCC M970016.

* * * * *